(12) United States Patent
Shiina

(10) Patent No.: US 8,034,947 B2
(45) Date of Patent: Oct. 11, 2011

(54) PYRIDINE OXIDE COMPOUND, AND PROCESS FOR PRODUCING CARBOXYLIC ACID DERIVATIVE AND OPTICALLY ACTIVE CARBOXYLIC ACID DERIVATIVE WITH THE USE OF THE SAME

(75) Inventor: Isamu Shiina, Tokyo (JP)

(73) Assignee: Tokyo University of Science Educational Foundation Administrative Organization, Tokyo (JP)

( * ) Notice: Subject to any disclaimer, the term of this patent is extended or adjusted under 35 U.S.C. 154(b) by 838 days.

(21) Appl. No.: 11/816,562

(22) PCT Filed: Feb. 17, 2006

(86) PCT No.: PCT/JP2006/302830
§ 371 (c)(1),
(2), (4) Date: Apr. 25, 2008

(87) PCT Pub. No.: WO2006/088132
PCT Pub. Date: Aug. 24, 2006

(65) Prior Publication Data
US 2009/0062548 A1    Mar. 5, 2009

(30) Foreign Application Priority Data

Feb. 18, 2005   (JP) ................................. 2005-042832

(51) Int. Cl.
C07D 213/22   (2006.01)
(52) U.S. Cl. ...................................................... 546/257
(58) Field of Classification Search .................... 546/257
See application file for complete search history.

(56) References Cited

FOREIGN PATENT DOCUMENTS

JP          07-133283        5/1995
JP          2003-335731      11/2003

OTHER PUBLICATIONS

Vippagunta et al., "Crystalline Solid", Advanced Drug Delivery Reviews 48 (2001) 3-26.*
Guillory (in Brittain ed.), "Polymorphism, etc.," NY: Marcel Dekker, Inc., 1999, 1-2, 183-226.*
Nakajima, Makoto et al., Enantioselective Michael additions of β-keto esters to a, β-unsaturated carbonyl compounds catalyzed by a chiral biquinoline N,N'-dioxide-scandium trifluoromethanesulfonate complex, Tetrahedron, Sep. 8, 2003, vol. 59, No. 37, p. 7307-7313.
Regnouf, de Vains, J. B. et al., New symmetric and unsymmetric polyfunctionalized 2,2'-bipyridines, Journal of Heterocyclic Chemistry, 1994, vol. 31, No. 4, p. 1069-77, see compound 12.
Sano, T. And Oriyama, T., "Development of catalytic asymmetric acylation of alcohols in the presence of a chiral 1, 2-diamine", Journal of Synthetic Organic Chemistry, 1999, 57 (7), pp. 598-607.
Shina, Isamu et al. "A New Condensation Reaction for the Synthesis of the Carboxylic Esters from Nearly Equimolar Amounts of Carboxylic Acids and Alcohols Using 2-Methyl-6-nitrobenzoic Anhydride" Chemistry Letters, Mar. 5, 2002, No. 3, pp. 286-287.
Written Opinion, PCT/JP2006/302830.

* cited by examiner

Primary Examiner — Patricia Morris
(74) Attorney, Agent, or Firm — Thomas, Kayden, Horstemeyer, Risley, LLP

(57) ABSTRACT

The invention relates to a pyridine oxide compound represented by formula (I), an optically active compound thereof, a salt thereof and a hydrate thereof, and, in the presence of the compound as a catalyst, performing 1) a method for producing an ester compound or an amide compound from a carboxylic acid equivalent and an alcohol or an amine, 2) an asymmetric esterification reaction or 3) an asymmetric amidation reaction. In formula (I), each $R^1$ may be the same as the other $R^1$ or different and each $R^1$ represents an alkyl group, an aromatic group, a heterocyclic group, a carboxyl group, an ester group, a cyano group, a halogen atom, an oxygen atom, a sulfur atom or a nitrogen atom; each $R^2$ may be the same as the other $R^2$ or different and each $R^2$ represents a hydrogen atom, an alkyl group, an aromatic group, a heterocyclic group, a carboxyl group, an ester group, a cyano group, a halogen atom, an oxygen atom or the like, and $R^3$ and $R^4$ may be the same or different and $R^3$ and $R^4$ each represent a hydrogen atom, an alkyl group, an aromatic group, a heterocyclic group, a carboxyl group, an ester group, a cyano group, a halogen atom, an oxygen atom or the like.

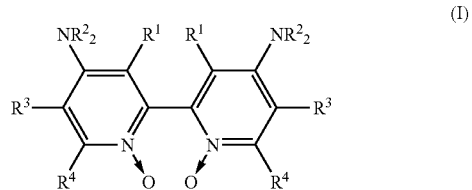

(I)

12 Claims, 1 Drawing Sheet

PYRIDINE OXIDE COMPOUND, AND PROCESS FOR PRODUCING CARBOXYLIC ACID DERIVATIVE AND OPTICALLY ACTIVE CARBOXYLIC ACID DERIVATIVE WITH THE USE OF THE SAME

TECHNICAL FIELD

The invention relates to a novel pyridine oxide compound useful as a catalyst, and a method for producing a compound using the pyridine oxide compound as a catalyst for acylation reactions and asymmetric acylation reactions.

BACKGROUND ART

Various catalysts have been developed and put into practice for advantageously implementing industrial synthesis of a variety of organic compounds.

However, many organic compounds, particularly pharmaceutical compounds and natural organic compounds, are optically active, and it has been difficult to artificially synthesize these compounds.

Accordingly, it is quite important to develop novel catalysts useful for the synthesis of these kinds of organic compounds.

Although metallic compounds have been developed as catalysts (see non-patent document 1), recent use of such catalysts has shown a negative trend due to problems of toxicity and environmental impact.

While amine catalysts have been developed in recent years as substitutes for metallic catalysts (see non-patent document 2), these catalysts are only able to be used for limited syntheses. Accordingly, there is a desire for the development of catalysts capable of being used in wide range of syntheses.

Non-patent document 1: "Synthesis of organic compounds VI: organic synthesis using metals", *Jikken Kagaku Koza* (*Handbook of Chemical Experiments*) (5th ed.), The Chemical Society of Japan, Maruzen, 2004, Vol. 18.

Non-patent document 2: Oriyama et al., (1999), "Development of catalytic asymmetric acylation of alcohols in the presence of a chiral 1,2-diamine", *Journal of Synthetic Organic Chemistry*, 1999, 57 (7).

DISCLOSURE OF INVENTION

Problems to be Solved by the Invention

Accordingly, an object of the invention is to develop a novel pyridine oxide compound useful as a catalyst and a method for producing a carboxylic acid derivative as well as an optically active organic compound using the pyridine oxide compound.

Means for Solving the Problem

The inventor of the invention has found, through investigations from such viewpoints, that a novel pyridine oxide compound represented by formula (I) below is useful as a catalyst.

The invention provides the followings.

<1> A compound represented by the following formula (I), an optically active compound thereof, a salt thereof or a hydrate thereof.

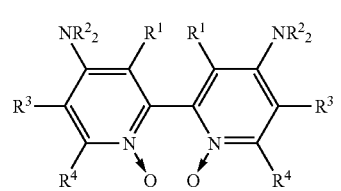

(I)

In formula (I), each $R^1$ may be the same as other $R^1$ or different, and each $R^1$ represents an alkyl group, an aromatic group, a heterocyclic group, a carboxyl group, an ester group, a cyano group, a halogen atom, an oxygen atom, a sulfur atom or a nitrogen atom; each $R^2$ may be the same as the other $R^2$ or different, and each $R^2$ represents an alkyl group, an aromatic group, a heterocyclic group, a carboxyl group, an ester group, a cyano group, a hydrogen atom, a halogen atom, an oxygen atom, a sulfur atom or a nitrogen atom; and $R^3$ and $R^4$ may be the same or different and $R^3$ and $R^4$ each represent an alkyl group, an aromatic group, a heterocyclic group, a carboxyl group, an ester group, a cyano group, a hydrogen atom, a halogen atom, an oxygen atom, a sulfur atom or a nitrogen atom.

<2> A compound represented by formula (Ia) or (Ib), a salt thereof or a hydrate thereof:

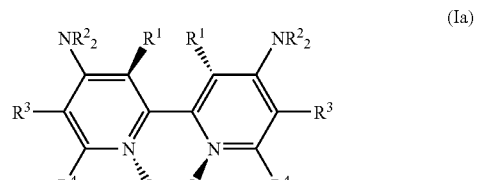

(Ia)

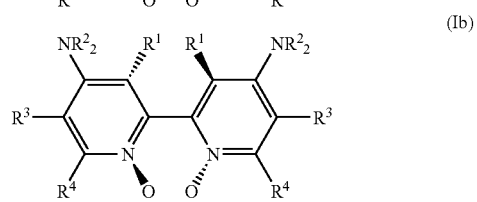

(Ib)

In the formulae, each $R^1$ may be the same as other $R^1$ or different, and each $R^1$ each represents an alkyl group, an aromatic group, a heterocyclic group, a carboxyl group, an ester group, a cyano group, a halogen atom, an oxygen atom, a sulfur atom or a nitrogen atom; each $R^2$ may be the same as the other $R^2$ or different, and each $R^2$ represents an alkyl group, an aromatic group, a heterocyclic group, a carboxyl group, an ester group, a cyano group, a hydrogen atom, a halogen atom, an oxygen atom, a sulfur atom or a nitrogen atom; and $R^3$ and $R^4$ may be the same or different and $R^3$ and $R^4$ each represent an alkyl group, an aromatic group, a heterocyclic group, a carboxyl group, an ester group, a cyano group, a hydrogen atom, a halogen atom, an oxygen atom, a sulfur atom or a nitrogen atom.

<3> A method for producing an ester compound or an amide compound from a carboxylic acid equivalent and an alcohol or an amine, wherein a reaction is performed in the presence of a compound according to (1) or (2) as a catalyst.

Effects of the Invention

It is possible to produce an ester compound, an amide compound or the like advantageously in an industrial scale by using the compound of the invention as a catalyst.

BEST MODE FOR CARRYING OUT THE INVENTION

Compound I

Figure 1:
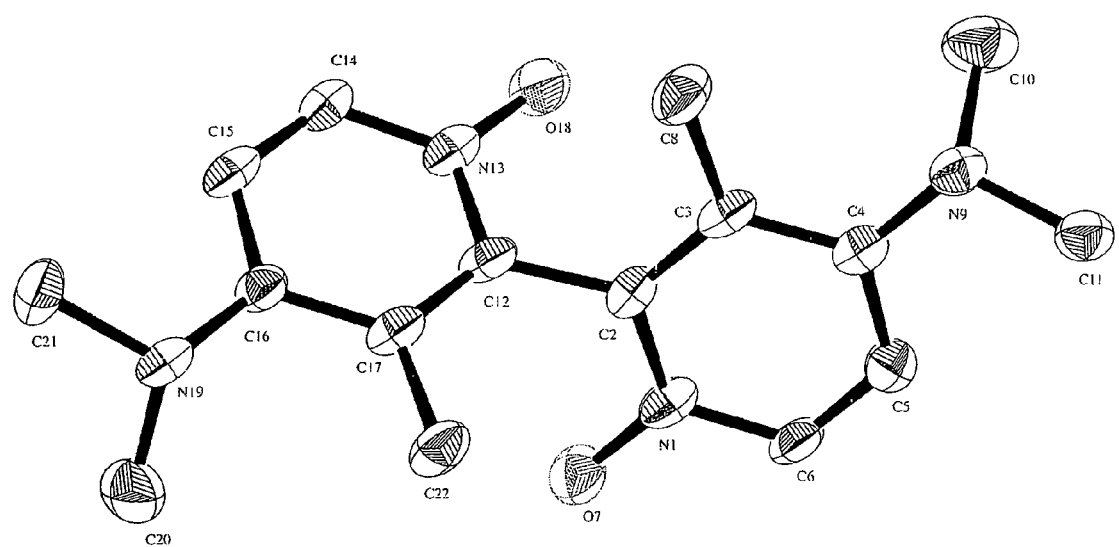
FIG. 1 shows the result of X-ray crystal analysis of the compound according to the invention.

The invention provides the compound represented by formula (I) above.

In formula (I), each $R^1$ may be the same as the other $R^1$ or different, and each $R^1$ represents an alkyl group, an aromatic group, a heterocyclic group, a carboxyl group, an ester group, a cyano group, a halogen atom, an oxygen atom, a sulfur atom or a nitrogen atom. The alkyl group is preferably an alkyl group having 1 to 8 carbon atoms, and specifically, the alkyl group is preferably a methyl group, an ethyl group, an n-propyl group, an isopropyl group, an n-butyl group, an isobutyl group, a sec-butyl group, a t-butyl group, an n-pentyl group, an isopentyl group, a neo-pentyl group, an n-hexyl group, an isohexyl group, an n-heptyl group, an n-octyl group or the like.

Each $R^2$ may be the same as the other $R^2$ or different, and each $R^2$ represents an alkyl group, an aromatic group, a heterocyclic group, a carboxyl group, an ester group, a cyano group, a hydrogen atom, a halogen atom, an oxygen atom, a sulfur atom or a nitrogen atom.

The alkyl group is preferably an alkyl group having 1 to 10 carbon atoms. Specifically, the alkyl group is preferably a methyl group, an ethyl group, an n-propyl group, an isopropyl group, an n-butyl group, an isobutyl group, a sec-butyl group, a t-butyl group, an n-pentyl group, an isopentyl group, a neo-pentyl group, an n-hexyl group, an isohexyl group, an n-heptyl group, an n-octyl group, an n-nonyl group, an n-decyl group or the like.

Examples of the aromatic group in $R^2$ include a phenyl group, a naphthyl group, an anthranyl group and the like.

Examples of the heterocyclic group include a pyridyl group, a pyrrole group, a furyl group, a thiophenyl group and the like.

Examples of the halogen atom include a fluorine atom, a chlorine atom, a bromine atom and an iodine atom.

$R^3$ and $R^4$ may be the same or different, and $R^3$ and $R^4$ each represent an alkyl group, an aromatic group, a heterocyclic group, a carboxyl group, an ester group, a cyano group, a hydrogen atom, a halogen atoms, an oxygen atom, a sulfur atom or a nitrogen atom.

Among these, the alkyl group is preferably an alkyl group having 1 to 10 carbon atoms. Specifically, the alkyl group is preferably a methyl group, an ethyl group, an n-propyl group, an isopropyl group, an n-butyl group, an isobutyl group, a sec-butyl group, a t-butyl group, an n-pentyl group, an isopentyl group, a neo-pentyl group, an n-hexyl group, an isohexyl group, an n-heptyl group, an n-octyl group, an n-nonyl group, an n-decyl group or the like.

Examples of the aromatic group in $R^3$ and $R^4$ include a phenyl group, a naphthyl group, an anthranyl group and the like.

Examples of the heterocyclic group include a pyridyl group, a pyrrole group, a furyl group and a thiophenyl group.

Examples of the halogen atom include a fluorine atom, a chlorine atom, a bromine atom and an iodine atom.

Specific examples of the compound represented by formula (I) include the following compounds:

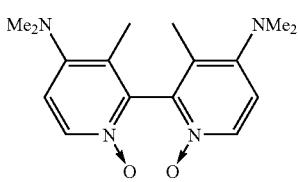

(1)

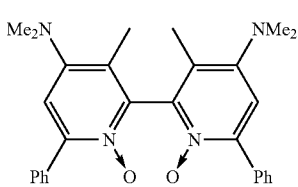

(2)

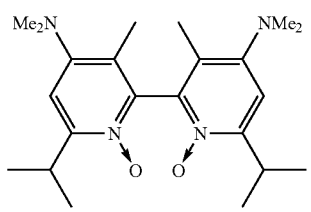

(3)

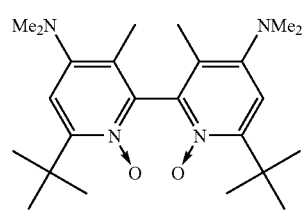

(4)

Among these, compound (2) or (3) is preferable as the catalyst.

The compounds represented by formula (I) include optically active compounds. Examples the optically active compounds include those represented by formula (Ia) or (Ib), where substituents $R^1$ to $R^4$ are the same as those in the compounds represented by formula (I).

Production Method

The compound represented by formula (I) may be produced according to the following equation:

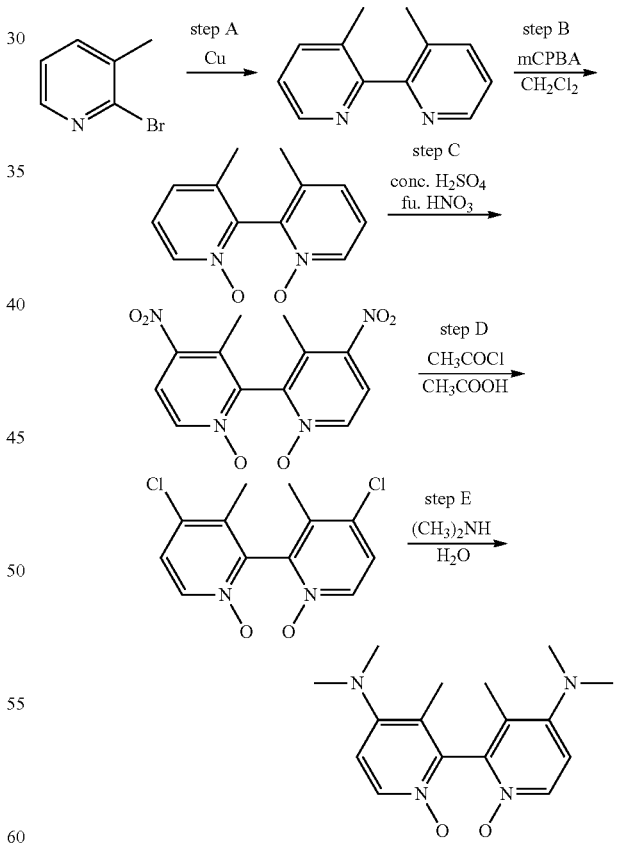

The production method will be described below with reference to the equation above.

Step A

2-Bromo-3-methylpyridine as the starting material is commercially available, for example, B 1894 available from Tokyo Kagaku Kogyo may be used.

Examples of the catalyst used in this step include copper, copper salts, palladium, palladium salts, nickel, nickel salts and the like.

The amount of the catalyst is preferably from about 10 mol % to 10 molar times of the amount of 2-bromo-3-methylpyridine. The copper catalyst is preferably used after washing with dilute nitric acid or the like.

The reaction is preferably performed by adding the catalyst to 2-bromo-3-methylpyridine as the starting material and is preferably performed at a temperature from 0 to 300° C. for 0.5 to 50 hours.

The product may be optionally purified by filtration, extraction and the like. Specific examples of the purification method include ion-exchange chromatography, column chromatography, recrystallization and the like.

Step B

Meta-chloroperbenzoic acid in an amount of 1 to 20 molar times of 3,3'-dimethyl-2,2'-bipyridyl is used. The solvent is preferably methylene chloride or 1,2-dichloroethane. The reaction temperature is preferably from −78 to 40° C., while the reaction time is preferably from 0.5 to 50 hours. The product may be optionally purified by a usual method.

Step C 3,3'-Dimethyl-2,2'-bipyridyl-N,N'-dioxide is nitrated in this step. The compound is preferably nitrated by a usual method by adding concentrated sulfuric acid and fuming nitric acid. The reaction temperature is preferably from 0 to 120° C., while the reaction time is preferably from 0.5 to 50 hours. The reaction mixture is preferably cooled with liquid nitrogen or the like after the reaction, and the desired product is preferably isolated by suction filtration while the reaction mixture is still chilled. After washing the solid product with cold water, the product is dried under reduced pressure to obtain 4,4'-dinitro-3,3'-dimethyl-2,2'-bipyridyl-N,N'-dioxide.

Step D

The nitro group of 4,4'-dinitro-3,3'-dimethyl-2,2'-bipyridyl-N,N'-dioxide is substituted with halogen in this step. Acetic chloride, sulfonic acid chloride or the like is preferably used for halogenation, and the amount of use thereof is preferably 1 to 500 molar times of 4,4'-dinitro-3,3'-dimethyl-2,2'-bipyridyl-N,N'-dioxide. The reaction temperature is preferably from 0 to 120° C., while the reaction time is preferably from about 0.5 to about 50 hours. The product may be purified by thin layer chromatography according to a usual method.

Step E

An amine compound is allowed to react with 4,4'-dinitro-3,3'-dimethyl-2,2'-bipyridyl-N,N'-dioxide, and a substituted amino group is introduced in this step. Examples of the amine compounds used in this step include ammonia (aqueous ammonia), dimethylamine, diethylamine and the like. The amine compound is preferably used in an amount from 1 to 500 molar times of the material. The reaction temperature is preferably from 0 to 300° C., while the reaction time is preferably from about 0.5 to about 50 hours. The product is purified by thin layer chromatography according to a usual method.

A compound represented by (Ia) or (Ib) which is an optically active compound of a compound represented by (I) of the invention may be obtained by resolution by column chromatography in which an optically active compound is supported, or by fractional recrystallization.

The compound represented by formula (I) and compounds represented by formulae (Ia) and (Ib) are effective as reaction catalysts, in particular as catalysts for esterification reaction, asymmetric esterification reaction and asymmetric amidation reaction.

Reaction products may be obtained in high yields in a reaction method implemented in the presence of the compound represented by formula (I) and the compound represented by formula (Ia) or (Ib) as a catalyst in (1) a method for producing an ester compound from an alcohol and a carboxylic acid; and in a reaction method implemented in the presence of the compound represented by formula (I) and the compound represented by formula (Ia) or (Ib) as a catalyst in (2) an asymmetric esterification reaction or (3) asymmetric amidation reaction.

In the method (1) for producing the ester compound, examples of the carboxylic acid include aliphatic carboxylic acids, α,β-unsaturated carboxylic acids, aromatic carboxylic acids and the like, while examples of the alcohol include aliphatic alcohols, α,β-unsaturated alcohols, aromatic alcohols and the like. Among these, the reaction between an aliphatic carboxylic acid and an aliphatic alcohol is preferable in terms of reactivity.

In the asymmetric esterification reaction (2), the reaction between a carboxylic acid, a carboxylic acid anhydride, a carboxylic acid halide or the like and an aliphatic alcohol, an α,β-unsaturated alcohol, an aromatic alcohols or the like is preferable. Among these, the reaction between a carboxylic acid anhydride and an aliphatic alcohol is preferable in terms of selectivity.

In the asymmetric amidation reaction (3), the reaction between a carboxylic acid, a carboxylic acid anhydride, a carboxylic acid halide or the like and a primary amine, a secondary amine or the like is preferable. Among these, the reaction between a carboxylic acid halide and a primary amine is preferable in terms of selectivity.

EXAMPLES

While the invention is described in detail with reference to examples, the invention is by no means restricted to these examples.

Example 1

A compound represented by formula (I) of the invention was synthesized according to the following reaction formula:

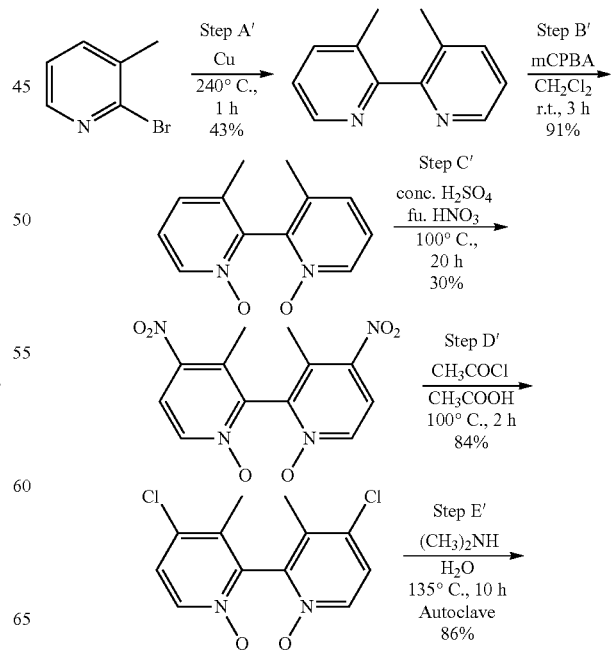

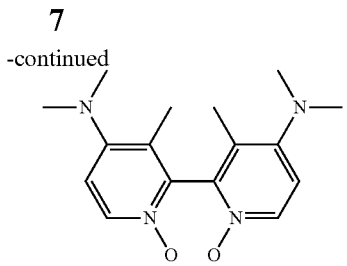

Step A'

Copper powder (8.1665 g) was washed with dilute aqueous nitric acid solution, and was transferred to a reaction vessel after roughly drying the powder. The copper powder was dried by heating with a heat gun (300° C.) under reduced pressure, and allowed to stand until the temperature is decreased to room temperature. 2-Bromo-3-methylpyridine (3.4 mL) was added to the reaction vessel, and the outside temperature of the reaction vessel was raised to 220° C. After increasing the outside temperature to 240° C. in 1 hour, the vessel was cooled to room temperature. The metal powder was dissolved by adding concentrated nitric acid, and the reaction solution was made to be weakly alkaline by adding aqueous 6 N sodium hydroxide solution. The reaction mixture was filtered through celite using ether as an elution solvent, and the filtrate was extracted three times with ether. The extract was concentrated under reduced pressure, and was purified by column chromatography (Merck silica gel 60, elution solvent; chloroform/methanol=30/1) to obtain 3,3'-dimethyl-2,2'-bipyridyl (1.862 g, 42.5%).

Step B'

Metachloroperbenzoic acid (2.9001 g) was added to a methylene chloride solution (28.9 mL) of 3,3'-dimethyl-2,2'-bipyridyl (1.1546 g) at room temperature. After stirring the reaction mixture at room temperature for 3 hours, the reaction mixture was filtered through an ion-exchange resin (strongly basic anion exchanger, DIAION SA11A) using methanol as an elution solvent. After concentrating the filtrate, the concentrated solution was purified by column chromatography (Merck silica gel 60, development solvent; chloroform/methanol=10/1→1/0) to obtain 3,3'-dimethyl-2,2'-bipyridyl-N,N'-dioxide (1.2267 g, 90.5%).

Step C'

Concentrated sulfuric acid (4.8 mL) and fuming nitric acid (1.7 mL) were added to 935.5 mg of 3,3'-dimethyl-2,2'-bipyridyl-N,N'-dioxide at 0° C. After stirring the solution at 100° C. for 20 hours, the reaction mixture was cooled to room temperature. Crushed ice (27 g) was added in advance to a vessel whose outside temperature was cooled to 0° C., and the reaction mixture was poured into the vessel followed by further cooling the reaction mixture by adding liquid nitrogen into the container. The product was isolated by suction filtration while the reaction mixture was still chilled, and the filtered solid was washed with cold water followed by drying under reduced pressure to obtain 4,4'-dinitro-3,3'-dimethyl-2,2'-bipyridyl-N,N'-dioxide (399.6 mg, 30.2%).

Step D'

Acetic acid (1.43 mL) and acetic acid chloride (0.96 mL) were added to 4,4'-dinitro-3,3'-dimethyl-2,2'-bipyridyl-N,N'-dioxide (100 mg) at room temperature. After stirring the reaction mixture at 100° C. for 2 hours, it was cooled to 0° C. The reaction mixture was poured onto 3 g of crushed ice, and was allowed to stand until the temperature is raised to room temperature. The reaction mixture was made to be weakly alkaline by adding aqueous 6 N sodium hydroxide solution. The reaction mixture was extracted with chloroform three times, and was purified by thin layer chromatography (Wako gel 60, development solvent: chloroform/methanol=10/1) to obtain 4,4'-dichloro-3,3'-dimethyl-2,2'-bipyridyl-N,N'-dioxide (78.1 mg, 84.2%).

Step E'

Water (0.48 mL) and 50% aqueous dimethylamine solution (7 mL) were added to 127.3 mg of 4,4'-dichloro-3,3'-dimethyl-2,2'-bipyrodyl-N,N'-dioxide in an autoclave. After stirring the mixture at 135° C. for 10 hours, it was cooled to room temperature. The reaction mixture was filtered through an ion-exchange resin (strongly basic anion-exchanger, DIAION SA11A) using methanol as an elution solvent. The filtrate was concentrated and purified by thin layer chromatography (Wako gel 60, development solvent: chloroform/methanol=5/1) to obtain 3,3'-dimethyl-4,4'-dimethylamino-2,2'-bipyridyl-N,N'-dioxide (DM-DMAPO: 116.7 mg, 86.1%).

The result of X-ray crystal analysis of the compound obtained through the steps A' to E' is shown in FIG. 1.

TABLE 1

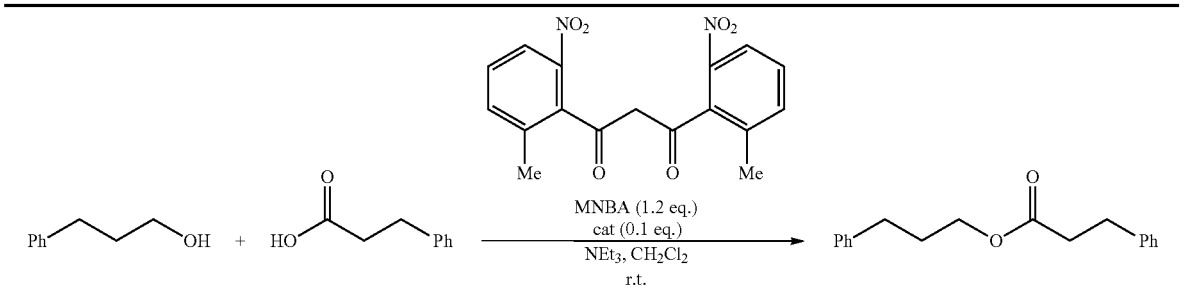

| Entry | Catalyst | Yield (%) | Recovery yield of starting material (%) |
|---|---|---|---|
| 1 | DMAP (a) | 81 | 13 |
| 2 | DMAPO (b) | 71 | — |
| 3 | Py-N-Oxide (c) | 1 | 35 |
| 4 | Dual-DMAPO (d) | 60 | 16 |
| 5 | 2,2'-bipyridyl-N,N'-dioxide (e) | 2 | 75 |
| 6 | 4,4'-dinitro-2,2'-bipyridyl-N,N'-dioxide (f) | 2 | 71 |

TABLE 1-continued
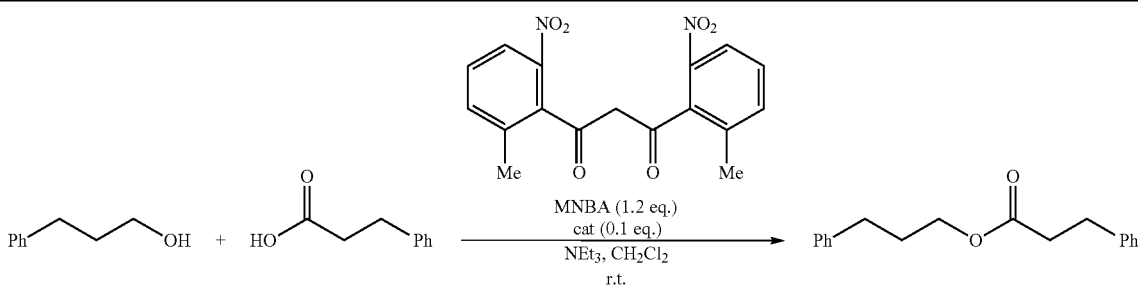
| Entry | Catalyst | Yield (%) | Recovery yield of starting material (%) |
|---|---|---|---|
| 7 | 4,4'-dichloro-2,2'-bipyridyl-N,N'-dioxide (g) | — | 75 |
| 8 | DM-DMAPO (h) (compound of the invention) | 84 | 4 |
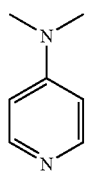
(a)
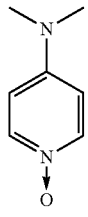
(b)
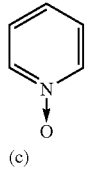
(c)
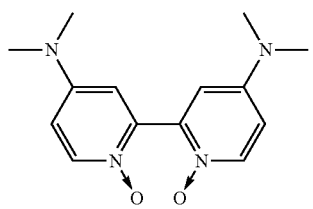
(d)
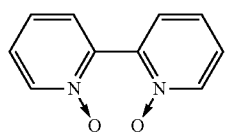
(e)

TABLE 1-continued

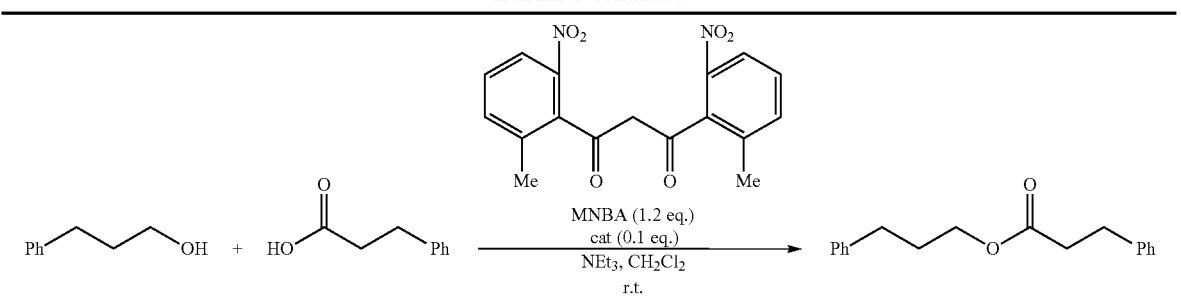

| Entry | Catalyst | Yield (%) | Recovery yield of starting material (%) |
|---|---|---|---|

(f)

(g)

(h)

Table 1 shows that the compound of the invention is useful as a catalyst of the esterification reaction.

Example 2

The following esterification reaction was performed using various catalysts (a) to (h).

A methylene chloride solution (1.5 mg) of DM-DMAPO (6.0 mg) was added to 250 mg of molecular sieves 4A that had been dried under reduced pressure in advance. A methylene chloride solution (1 mL) of triethylamine (44.5 mg) and a methylene chloride solution (3 mL) of 2-methyl-6-nitrobenzoic acid anhydride (82.9 mg) and 3-phenylpropionic acid (37.1 mg) were added to the above-mentioned mixture at room temperature. After stirring the reaction mixture at room temperature for 10 minutes, a methylene chloride solution (1.5 mL) of 3-phenylpropanol (27.9 mg) was added at room temperature. The reaction was stopped by adding a saturated aqueous solution of ammonium chloride after stirring the mixture for 24 hours at room temperature, and the reaction mixture was extracted three times with methylene chloride. The organic layer was washed with saturated aqueous sodium bicarbonate solution, water and saturated aqueous sodium chloride solution, and the organic layer was dried over anhydrous sodium sulfate. The organic layer was concentrated under reduced pressure, and thereafter was purified by thin layer chromatography (Wako gel 60, development solvent: hexane/ethyl acetate=3/1) to obtain 3-phenylpropionoc acid 3-phenylpropyl (46.3 mg, 84%).

TABLE 2

Asymmetric esterification

| entry | R | ester | | alcohol | |
| | | yield(%) | ee(%) | yield(%) | ee(%) |
|---|---|---|---|---|---|
| 1 | $^i$Pr | 17 | 14 | 54 | 4 |
| 2$^a$ | $^t$Bu | 27 | 19 | 55 | 9 |

$^a$Reaction Conditions: (S)-DM-DMAPO (10 mol %), Piv$_2$O (3.0 eq.).

Table 2 shows that, when the compound of the invention is used as the catalyst and pivalic acid anhydride is used as an acylation agent in the asymmetric esterification reaction, the enantiomer excess ratio of the ester obtained is as high as 19%.

Example 3

Triethylamine (37.9 mg), (S)-DM-DMAPO (15.2 mg) and pivalic acid anhydride (279.4 mg) were added to 62.2 mg of 1-phenethyl alcohol dissolved in 2 mL of methylene chloride. After stirring the solution for 1 week at room temperature, the reaction was stopped by adding saturated aqueous ammonium chloride solution, and the reaction mixture was extracted three times with methylene chloride. The organic layer was washed with saturated aqueous sodium bicarbonate solution, water and saturated aqueous sodium chloride solution, and was dried over anhydrous sodium sulfate. The organic layer was concentrated under reduced pressure, and thereafter was purified by thin layer chromatography (Wako gel 60, development solvent: hexane/ethyl acetate=3/1) to obtain pivalic acid 1-phenethyl (28.6 mg, 27%, 19% ee).

TABLE 3

Asymmetric amidation reaction

| entry | reagent | amine | time(h) | yield(%) | ee(% ee) |
|---|---|---|---|---|---|
| 1 | PivCl | Et$_3$N | 1 | 33 | 3 |
| 2 | TCBC | — | 2 | 44 | 18 |

Table 3 shows that, when the compound of the invention is used as the catalyst and 2,4,6-trichlorobenzoic acid chloride (TCBC) as an acylation agent in the asymmetric amidation reaction, the enantiomer excess ratio of the amide obtained is as high as 18%.

Example 4

A methylene chloride solution (1 mL) of (S)-DM-DMAPO (2.7 mg) and 2,4,6-trichlorobenzoic acid chloride (25.3 mg) were added at −78° C. to 24.5 mg of 1-phenethylamine dissolved in 1 mL of methylene chloride. After stirring the solution at −78° C. for 2 hours, the reaction was stopped by adding saturated aqueous sodium bicarbonate solution, and the reaction mixture was extracted three times with methylene chloride. The organic layer was washed with water and saturated aqueous sodium chloride solution, and was dried over anhydrous sodium sulfate. The organic layer was concentrated under reduced pressure and thereafter was purified by thin layer chromatography (Wako gel 60, development solvent: hexane/ethyl acetate=2/1) to obtain 2,4,6-trichlorobenzoic acid 1-phenethylamide (29.4 mg, 44%, 18% ee).

TABLE 4

Asymmetric amidation reaction (asymmetrization reaction)

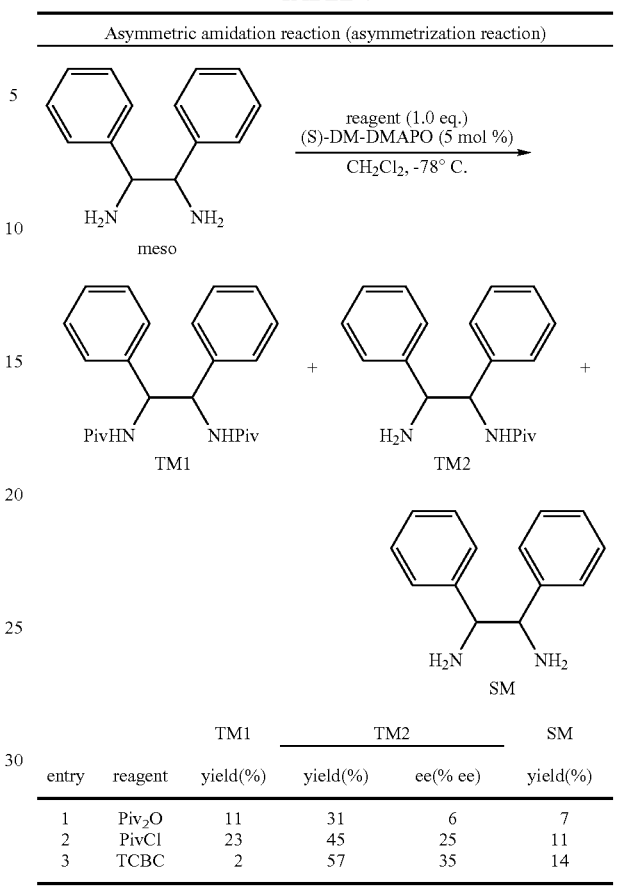

| entry | reagent | TM1 yield(%) | TM2 yield(%) | TM2 ee(% ee) | SM yield(%) |
|---|---|---|---|---|---|
| 1 | Piv$_2$O | 11 | 31 | 6 | 7 |
| 2 | PivCl | 23 | 45 | 25 | 11 |
| 3 | TCBC | 2 | 57 | 35 | 14 |

Table 4 shows that, when the compound of the invention was used as the catalyst and 2,4,6-trichlorobenzoic acid chloride (TCBC) is used in the asymmetric amidation reaction, the enantiomer excess ratio of the monoamide (TM2) obtained is as high as 35%.

Example 5

A methylene chloride solution (1 mL) of 2.7 mg of (S)-DM-DMAPO and 48.2 mg of 2,4,6-trichlorobenzoic acid chloride was added at −78° C. to 42.6 mg of meso-1,2-diphenyl ethylenediamine dissolved in 1 mL of methylene chloride. After stirring the mixture for 1 hour at −78° C., the reaction was stopped by adding saturated aqueous sodium bicarbonate solution. The reaction mixture was extracted three times with methylene chloride. The organic layer was washed with water and saturated aqueous sodium chloride solution, and was dried over anhydrous sodium sulfate. The organic layer was concentrated under reduced pressure and thereafter was purified by thin layer chromatography (Wako gel 60, development solvent: chloroform/methanol=15/1) to obtain 2,4,6-trichlorobenzoic acid monoamide of 1,2-diphenethylethylenediamine (48.0 mg, 57%, 35% ee).

INDUSTRIAL APPLICABILITY

By using the compound of the invention as a catalyst in the production of ester compounds, asymmetric ester reactions and asymmetric amidation reactions, high-yield, industrially advantageous production is possible.

The invention claimed is:

1. A compound represented by formula (I), an optically active compound thereof or a salt thereof:

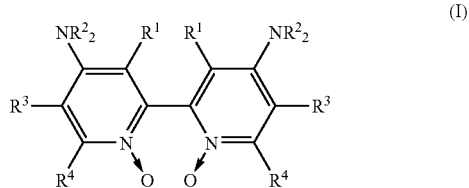

wherein, in formula (I), each $R^1$ may be the same as the other $R^1$ or different, and each $R^1$ represents an alkyl group, a carboxyl group, a cyano group or a halogen atom; each $R^2$ may be the same as the other $R^2$ or different, and each $R^2$ represents an alkyl group, a carboxyl group, a cyano group, a hydrogen atom or a halogen atom; and $R^3$ and $R^4$ may be the same or different and $R^3$ and $R^4$ each represent an alkyl group, a carboxyl group, a cyano group, a hydrogen atom or a halogen atom.

2. A compound represented by formula (Ia) or (Ib) or a salt thereof

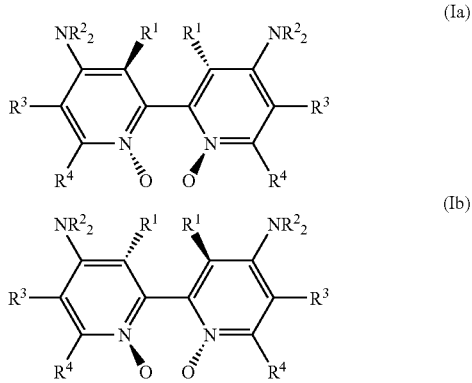

wherein, in formulae, each $R^1$ may be the same as the other $R^1$ or different, and each $R^1$ represents an alkyl group a carboxyl group, a cyano group or a halogen atom; each $R^2$ may be the same as the other $R^2$ or different, and each $R^2$ represents an alkyl group, a carboxyl group, a cyano group or a hydrogen atom; and $R^3$ and $R^4$ may be the same or different and $R^3$ and $R^4$ each represent an alkyl group, a carboxyl group, a cyano group or a hydrogen atom.

3. A method for producing an ester compound or an amide compound, the method comprising performing a reaction in the presence of a compound according to claim 1 as a catalyst in (1) a method for producing an ester compound or an amide compound from a carboxylic acid equivalent and an alcohol or an amine, (2) an asymmetric esterification reaction or (3) an asymmetric amidation reaction.

4. A method for producing an ester compound or an amide compound, the method comprising performing a reaction in the presence of a compound according to claim 2 as a catalyst in (1) a method for producing an ester compound or an amide compound from a carboxylic acid equivalent and an alcohol or an amine, (2) an asymmetric esterification reaction or (3) an asymmetric amidation reaction.

5. The compound according to claim 1, wherein in formula (I), each $R^1$ may be the same as the other $R^1$ or different, and each $R^1$ represents an alkyl group; each $R^2$ may be the same as the other $R^2$ or different, and each $R^2$ represents an alkyl group; and $R^3$ and $R^4$ each represent a hydrogen atom.

6. The compound according to claim 2, wherein in formulae, each $R^1$ may be the same as the other $R^1$ or different, and each $R^1$ represents an alkyl group; each $R^2$ may be the same as the other $R^2$ or different, and each $R^2$ represents an alkyl group; and $R^3$ and $R^4$ each represent a hydrogen atom.

7. The compound according to claim 1, wherein in formula (I), each $R^1$ represents a methyl group; each $R^2$ represents a methyl group; and $R^3$ and $R^4$ each represent a hydrogen atom.

8. The compound according to claim 2, wherein in formulae, each $R^1$ represents a methyl group; each $R^2$ represents a methyl group; and $R^3$ and $R^4$ each represent a hydrogen atom.

9. The method according to claim 3, wherein in formula (I), each $R^1$ may be the same as the other $R^1$ or different, and each $R^1$ represents an alkyl group; each $R^2$ may be the same as the other $R^2$ or different, and each $R^2$ represents an alkyl group; and $R^3$ and $R^4$ each represent a hydrogen atom.

10. The method according to claim 4, wherein in formulae, each $R^1$ may be the same as the other $R^1$ or different, and each $R^1$ represents an alkyl group; each $R^2$ may be the same as the other $R^2$ or different, and each $R^2$ represents an alkyl group; and $R^3$ and $R^4$ each represent a hydrogen atom.

11. The method according to claim 3, wherein in formula (I), each $R^1$ represents a methyl group; each $R^2$ represents a methyl group; and $R^3$ and $R^4$ each represent a hydrogen atom.

12. The method according to claim 4, wherein in formulae, each $R^1$ represents a methyl group; each $R^2$ represents a methyl group; and $R^3$ and $R^4$ each represent a hydrogen atom.

* * * * *